(12) United States Patent  
Shimizu et al.

(10) Patent No.: US 8,905,544 B2  
(45) Date of Patent: Dec. 9, 2014

(54) OPHTHALMIC APPARATUS

(71) Applicant: Nidek Co., Ltd., Aichi (JP)

(72) Inventors: Kazunari Shimizu, Aichi (JP); Hiroyuki Hiramatsu, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 14/319,727

(22) Filed: Jun. 30, 2014

(65) Prior Publication Data

US 2014/0313481 A1 Oct. 23, 2014

Related U.S. Application Data

(63) Continuation of application No. 13/118,672, filed on May 31, 2011, now Pat. No. 8,801,181.

(30) Foreign Application Priority Data

May 31, 2010 (JP) .................................. 2010-124511

(51) Int. Cl.
*A61B 3/14* (2006.01)
*A61B 3/10* (2006.01)
*A61B 3/117* (2006.01)
*A61B 3/00* (2006.01)
*A61F 2/16* (2006.01)

(52) U.S. Cl.
CPC ........ *A61B 3/0058* (2013.01); *A61F 2002/1697* (2013.01); *A61B 3/117* (2013.01); *A61B 3/0033* (2013.01); *A61F 2/1662* (2013.01)
USPC ............ 351/206; 351/205; 351/210; 351/221

(58) Field of Classification Search
USPC ......... 351/206, 205, 210, 221, 200, 246, 212, 351/214, 247
See application file for complete search history.

(56) References Cited

U.S. PATENT DOCUMENTS

| 6,033,075 | A | 3/2000 | Fujieda et al. |
| 6,467,906 | B1 | 10/2002 | Alpins |
| 7,331,667 | B2 | 2/2008 | Grotehusmann et al. |
| 7,891,811 | B2 | 2/2011 | Graether |
| 2006/0028619 | A1 | 2/2006 | Fujieda et al. |

(Continued)

FOREIGN PATENT DOCUMENTS

| JP | 11276437 | 10/1999 |
| JP | 2006026242 | 2/2006 |
| JP | 200945461 | 3/2009 |
| JP | 2012506272 | 3/2012 |

OTHER PUBLICATIONS

US Office Action dated Dec. 20, 2011 filed in the parent U.S. Appl. No. 13/118,672.

(Continued)

*Primary Examiner* — Dawayne A Pinkney
(74) *Attorney, Agent, or Firm* — Rankin, Hill & Clark LLP

(57) ABSTRACT

An ophthalmic apparatus for guiding positioning an intraocular lens for astigmatism correction, includes: an obtaining unit for obtaining an anterior segment image of a patient's eye and an astigmatic axis of a patient's cornea; a feature point designating unit for defining a feature point of an iris or a sclera on the anterior segment image; and a display control unit for superimposing and displaying a gauge image that models a cornea gauge and an axis that represents the astigmatic axis of the cornea on the anterior segment image.

5 Claims, 5 Drawing Sheets

(56) References Cited

U.S. PATENT DOCUMENTS

2009/0048608 A1 2/2009 Boukhny et al.
2011/0075098 A1 3/2011 Endo et al.
2011/0230751 A1 9/2011 Kersting

OTHER PUBLICATIONS

US Office Action dated Apr. 24, 2012 filed in the parent U.S. Appl. No. 13/118,672.
US Office Action dated Jun. 25, 2012 filed in the parent U.S. Appl. No. 13/118,672.

OPHTHALMIC APPARATUS

CROSS-REFERENCE TO RELATED APPLICATION

This application is based on Japanese Patent Application No. 2010-124511 filed with the Japan Patent Office on May 31, 2010, the entire content of which is hereby incorporated by reference.

BACKGROUND

1. Technical Field

The embodiments disclosed herein relate to an ophthalmic apparatus for injecting and installing in a patient's eye an intraocular lens for astigmatism correction to be used in an intraocular lens injecting operation such as a cataract operation.

2. Related Art

An apparatus that obtains measurement data of a wide-range eye refractive power distribution (including wavefront aberration) of a patient's eye (examinee's eye) and measurement data of a cornea shape distribution and displays the respective measurement data as color maps is known (for example, refer to JP-A-11-276437 (corresponding to U.S. Pat. No. 6,033,075) and JP-A-2006-26242 (corresponding to U.S. Patent Publication No. 2006/028619 A1)). These measurement data are used to determine dioptic power and the like of an intraocular lens (IOL) to be used in an intraocular lens injecting operation such as a cataract operation.

Also, a technique to instruct an incision site and the like to be formed on a patient's eye when an IOL is to be injected in the patient's eye (technique to create a guide for installation (positioning) of the IOL) is known (for example, refer to JP-A-2009-45461 (corresponding to U.S. Patent Publication No. 2009/0468608 A1)).

SUMMARY

An ophthalmic apparatus for guiding positioning an intraocular lens for astigmatism correction, includes: an obtaining unit for obtaining an anterior segment image of a patient's eye and an astigmatic axis of a patient's cornea; a feature point designating unit for defining a feature point of an iris or a sclera on the anterior segment image; and a display control unit for superimposing and displaying a gauge image that models a cornea gauge and an axis that represents the astigmatic axis of the cornea on the anterior segment image.

BRIEF DESCRIPTION OF THE DRAWINGS

The foregoing and other objects, features, aspects and advantages of the embodiments will become more apparent from the following detailed description when taken in conjunction with the accompanying drawings, in which.

DESCRIPTION OF EMBODIMENTS

Figure 1:
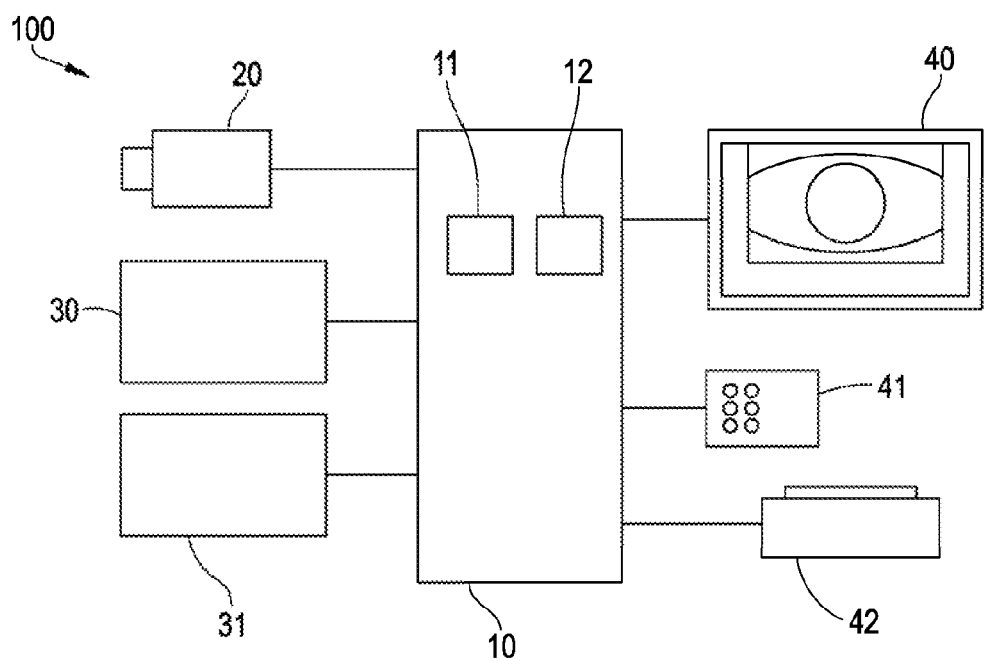
FIG. 1 is a block diagram illustrating a schematic configuration of a first embodiment of an ophthalmic apparatus.

The embodiments will be described below with reference to the accompanying drawings, in which like reference characters designate similar or identical parts throughout the several views thereof.

Recently, an IOL for astigmatism correction (toric IOL) has been used. Such a toric IOC is installed in a patient's eye along an astigmatic axis of the patient's eye. In a case where the toric IOL is to be injected and installed in the patient's eye, an operator places a guide member referred to as a cornea gauge in which scale marks are provided on a ring-like member around (outside) a corneal ring of the patient's eye. The operator uses this guide member and performs an operation while recognizing the astigmatic axis of the patient's eye. The scale marks of the cornea gauge are provided with numbers representing angles. A scale mark of a 0-degree angle of the cornea gauge is aligned with a horizontal axis of the patient's eye. However, in a case where the cornea gauge is moved, or the patient's eye is tortured during the operation, the horizontal axis of the patient's eye will be misaligned with the scale mark of the 0-degree angle of the cornea gauge. It is difficult for the operator to figure out this misalignment amount.

Also, in some cases, an axis of the IOL is positioned to correspond to the astigmatic axis of the patient's eye after the operation (after installation of the IOL). In this case, guide information representing the relationship between the axis of the IOL and the astigmatic axis of the patient's eye will make the positioning of the IOL by the operator easy.

A technical problem on an ophthalmic apparatus is to provide an ophthalmic apparatus that enables efficient positioning and installation of an IOL for astigmatism correction to and in a patient's eye.

One aspect of the present embodiment includes the following configuration.

An ophthalmic apparatus for guiding positioning an intraocular lens for astigmatism correction, includes: an input unit for inputting an anterior segment image of a patient's eye and an astigmatic axis of a patient's cornea; a feature point designating unit for defining a feature point of an iris or a sclera on the anterior segment image; and a display control unit for superimposing and displaying a gauge image that models a cornea gauge and an axis that represents the astigmatic axis of the cornea on the anterior segment image.

According to this aspect, positioning and installation of a toric IOL to and in a patient's eye can be performed efficiently.

A first embodiment of an ophthalmic apparatus will be described below based on the drawings. FIG. 1 is a block diagram illustrating a schematic configuration of an ophthalmic apparatus 100 according to the first embodiment.

The ophthalmic apparatus 100 is an apparatus that performs measurement (analysis) of an eye refractive power distribution and measurement (analysis) of a cornea shape distribution. The ophthalmic apparatus 100 is also an apparatus that performs obtaining, management, image processing (process), display output (print), and the like of the measurement (analysis) data and the like.

The ophthalmic apparatus 100 includes a control unit 10. The control unit 10 is a member to perform control of the entire apparatus (mechatronic control and the like), measurement (analysis) of the eye refractive power distribution, measurement (analysis) of the cornea shape distribution, and obtaining, management, image processing (process), display, output (print), and the like of the measurement (analysis) data and the like. The control unit 10 is connected to a camera 20, a measurement portion 30, a movement mechanism portion 31, a monitor 40, an operation portion 41, a printer 42 or the like. The camera 20 is an imaging unit (obtaining unit) that includes an imaging optical system for obtaining an anterior segment image of a patient's eye (examinee's eye). The measurement portion 30 has a measuring optical system having a light source for measurement, a light receiving device for measurement, and other optical devices. The movement mechanism portion 31 has a mechatronic mechanism constituted by a motor and the like. By use of this mechatronic mechanism, the movement mechanism portion 31 moves the camera 20 and the measurement portion 30 with respect to the patient's eye for alignment and the like. The monitor 40 displays the anterior segment image, the measurement (analysis) data, and the like. The operation portion 41 has a switch, a pointing device (feature point designating unit), and the like for inputting operation signals to the apparatus. The printer 42 prints the anterior segment image, the measurement (analysis) data, and the like. It is to be noted that the ophthalmic apparatus 100 as the first embodiment has a GUI (graphical user interface) function. Also, the monitor 40 in the first embodiment has a touch panel function. By pressing a switch or the like arranged (displayed) on the screen of the monitor 40, an operation signal is input in the control unit 10.

The control unit 10 has firmware that performs control of the respective hardware included in the ophthalmic apparatus 100. The control unit 10 also has a board computer that performs analysis, management, image processing (process), and the like. The control unit 10 further has a memory 11, an image processing unit 12, and the like. The memory 11 stores setting information of the entire apparatus, measurement (analysis) results by the measurement portion 30, the anterior segment image, and the like. The image processing unit 12 is a unit for displaying the anterior segment image, the measurement (analysis) data, and the like on the monitor 40.

The control unit 10 illuminates an anterior segment of the patient's eye by an illumination light from an anterior segment illuminating light source provided on the measurement portion 30. The control unit 10 obtains its reflection light by use of the camera 20. In this manner, the control unit 10 obtains an anterior segment image. Also, the control unit 10 illuminates the anterior segment by illumination lights from plural ring image forming light sources provided on the measurement portion 30. The control unit 10 then performs image processing and analysis of an anterior segment image containing the ring images captured by the camera 20. In this manner, the control unit 10 obtains the cornea shape distribution of the patient's eye, an astigmatic axis of the patient's eye, a pupil center position of the patient's eye (anterior segment image), and the like. It is to be noted that the astigmatic axis of the patient's eye is derived from a cornea curvature (kerato value). Accordingly, "the astigmatic axis of the patient's eye" in this specification represents an astigmatic axis of the cornea.

Here, an angle of the astigmatic axis is calculated and displayed with reference to the horizontal axis of the patient's eye. The horizontal axis of the patient's eye represents a horizontal axis in the eye of the patient in a sitting position. The horizontal axis of the patient's eye corresponds to a 0-degree meridian of the patient's eye.

Also, a reflection light obtained by reflection of a measurement light from a measuring light source provided on the measurement portion 30 on a fundus of the patient's eye is received at the light receiving device. The control unit 10 performs image processing and analysis of the light receiving result to obtain the eye refractive power distribution of the patient's eye.

Also, the control unit 10 analyzes eye refractive power distribution data and cornea shape distribution data. Based on the analysis result, the control unit 10 then creates color maps (an eye refractive power distribution map and a cornea shape distribution map) to facilitate visible recognition of the respective measurement (analysis) data. The eye refractive power distribution map (image) is one in which distribution of spherical dioptic powers, cylindrical dioptic powers, and the like is separated by color per predetermined dioptic power level. On the other hand, the cornea shape distribution map (image) is one in which distribution of cornea refractive powers obtained by conversion of the cornea curvatures (curvature radii) is separated by color per predetermined dioptic power level.

Figure 2A:
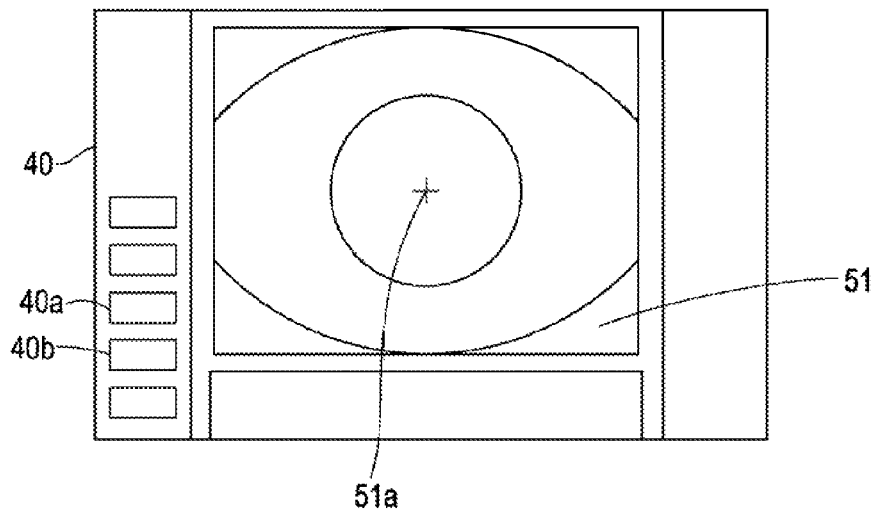
FIG. 2A illustrates an anterior segment display on a monitor.
Figure 2B:
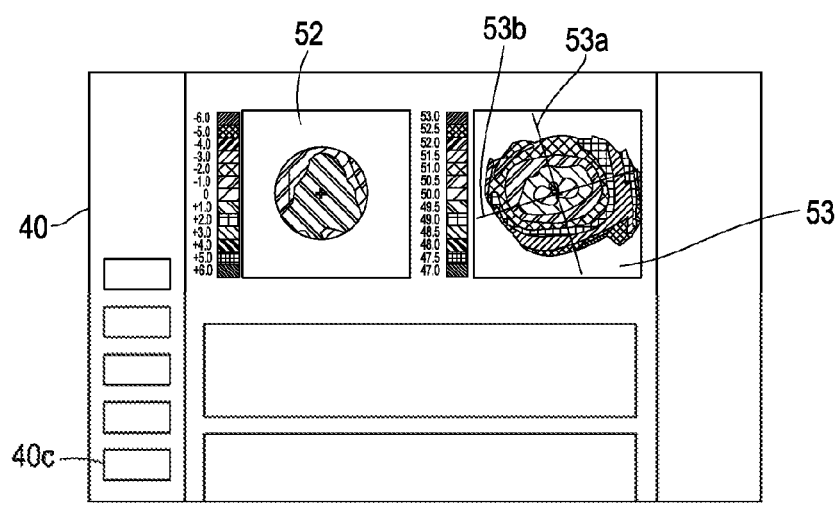
FIG. 2B illustrates a map display on the monitor.

Next, measurement and analysis operations of the ophthalmic apparatus 100 will be described with reference to contents displayed on the monitor 40. FIGS. 2A and 2B illustrate contents displayed on the monitor 40.

When a power switch of the ophthalmic apparatus 100 is pressed (powered), the control unit 10 captures (images) anterior segment images of the patient's eye sequentially by use of the camera 20. Thereafter, the control unit 10 makes the anterior segment images displayed on the monitor 40 as a real-time moving image. When a measurement switch 40a for inputting a measurement start signal displayed on the monitor 40 is pressed, the control unit 10 controls driving of the movement mechanism portion 31 based on the anterior segment images for alignment and the like of the camera 20 and the measurement portion 30. When the alignment is finished, the control unit 10 controls driving of the measurement portion 30 to project a measurement light to the fundus of the patient's eye. The control unit 10 then receives the measurement light reflected on the fundus at the light receiving device to obtain the eye refractive power distribution of the patient's eye. Also, the control unit 10 controls driving of the measurement portion 30 to project (form) ring images on the cornea of the patient' eye. The control unit 10 then captures (images) an anterior segment image containing the ring images by the camera 20. Based on the image, the control unit 10 obtains the cornea shape distribution of the patient's eye, the astigmatic axis of the patient's eye, the pupil center position of the patient's eye (anterior segment image), and the like. It is to be noted that the astigmatic axis data in the first embodiment includes a dioptic power and an axial angle of a strong principal meridian and a dioptic power and an axial angle of a weak principal meridian. The control unit 10 then makes an anterior segment image 51 clipped as a still image displayed on the monitor 40 (refer to FIG. 2A). The control unit 10 also makes a pupil center position 51a of the anterior segment image 51 displayed to be superimposed. The anterior segment image data, astigmatic axis data, pupil center position data, and the like are stored in the memory 11.

Subsequently, when an analysis switch 40b for inputting an analysis start signal displayed on the monitor 40 is pressed, the control unit 10 obtains eye refractive power distribution data. The control unit 10 then obtains an eye refractive power distribution map (image) 52 made by mapping the eye refractive power distribution under predetermined conditions. Also, the control unit 10 obtains cornea shape distribution data and a cornea shape distribution map (image) 53 made by mapping the cornea shape distribution under predetermined conditions. The control unit 10 then makes the maps 52 and 53 displayed on the monitor 40 (refer to FIG. 2B). On the map 53 are displayed to be superimposed a strong principal meridian (astigmatic axis line) 53a and a weak principal meridian (astigmatic axis line) 53b of the astigmatic axis obtained from the cornea shape distribution data. The eye refractive power distribution data, cornea shape distribution data, maps 52 and 53, and the like are stored in the memory 11.

Subsequently, when a guide creation switch 40c for inputting a guide creation start signal displayed on the monitor 40 is pressed, the control unit 10 makes a guide creation screen 60 (refer to FIGS. 3A to 3C) displayed on the monitor 40. A guide in the first embodiment possesses astigmatic axis information that enables an operator to recognize the astigmatic axis of the patient's eye easily during an IOL injecting operation. More specifically, the guide instructs a reference position for placing a cornea gauge at the anterior segment of the patient's eye. The operator determines a position to place the cornea gauge with reference to the reference position. This enables the operator to recognize the astigmatic axis of the patient's eye indirectly from scale marks of the cornea gauge. With reference to the guide, the operator injects and installs a toric IOL in a crystalline lens capsule from which a crystalline lens has been removed. At this time, the operator can align (position) the astigmatic axis of the patient's eye with (to) an axis of the IOL. On the guide, useful information for the IOL injecting operation is selected and displayed. Accordingly, the guide is also referred to as a summary. In the first embodiment, an image displayed on the guide creation screen 60 is a guide image.

Meanwhile, the anterior segment image of the patient's eye imaged before the operation is imaged in a state where the patient is in a seated position. In the actual operation, the patient is in a supine position (state where the patient lies face upward on an operating table). This causes torsion of the patient's eye and torsion of the astigmatic axis. Hence, it is preferable to enable to confirm by the guide the reference position of the patient's eye that does not move against the eyeball.

Figure 3A:
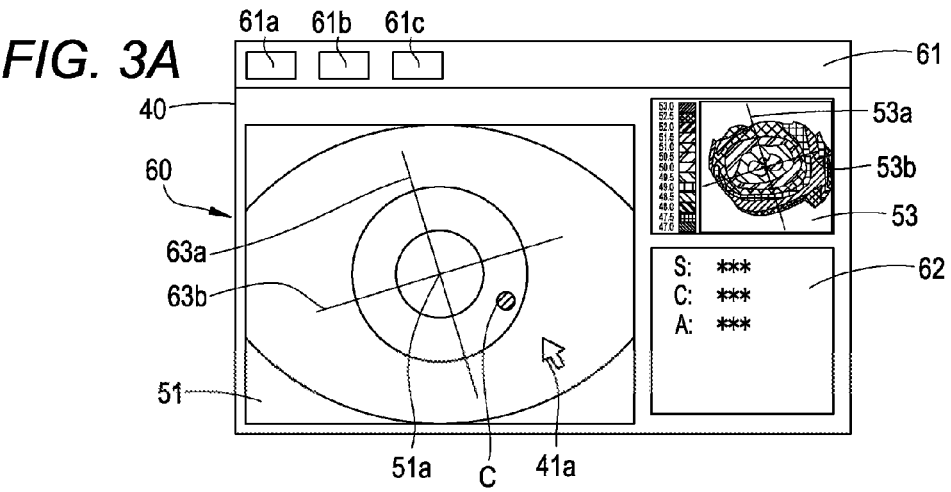
FIG. 3A illustrates a guide creation screen on which an anterior segment image is displayed.

On the guide creation screen 60 illustrated in FIG. 3A are displayed a bar 61 on which switches are arranged, the anterior segment image 51 of the patient's eye obtained (input) in advance, the cornea shape distribution map 53, and a display box 62 for measurement (analysis) data and the like.

The anterior segment image 51 is displayed in an image size that allows the operator to visibly recognize feature points inside and outside a corneal ring. The map 53 is displayed in an image size that allows recognition of the strong principal meridian 53a and the weak principal meridian 53b and that does not interfere with the display of the anterior segment image 51. On the anterior segment image 51 are displayed to be superimposed a strong principal meridian and a weak principal meridian of the astigmatic axis of the patient's eye obtained (input) in advance. A strong principal meridian (astigmatic axis line) 63a and a weak principal meridian (astigmatic axis line) 63b are displayed in different colors such that the operator can visibly recognize them easily. For example, the strong principal meridian 63a is displayed in red while the weak principal meridian 63b is displayed in blue. Meanwhile, the strong principal meridian 53a and the weak principal meridian 53b are displayed on the map 53 as well. Thus, the operator can evaluate reliability of the astigmatic axis data easily by referring to the map 53, which shows the cornea shape distribution. The ophthalmic apparatus 100 is configured to align the axis of the IOL with the strong principal meridian of the patient's eye.

On the display box 62 are displayed the dioptic power, the axial angle, and the like of the astigmatic axis of the patient's eye obtained (input) in advance. On the bar 61 are displayed a switch 61a, a switch 61b, and a switch 61c. The switch 61a is a switch to superimpose and display a cornea gauge image 70 that models the cornea gauge. The switch 61b is a switch to store the guide (gauge image) created on the guide creation screen 60. The switch 61c is a switch to print the guide (gauge image) displayed on the guide creation screen 60. Also, on the guide creation screen 60 is displayed a cursor 41a of the pointing device of the operation portion 41. It is to be noted that the cursor 41a may be configured to move to link with a touch position on the monitor 40.

Figure 3B:
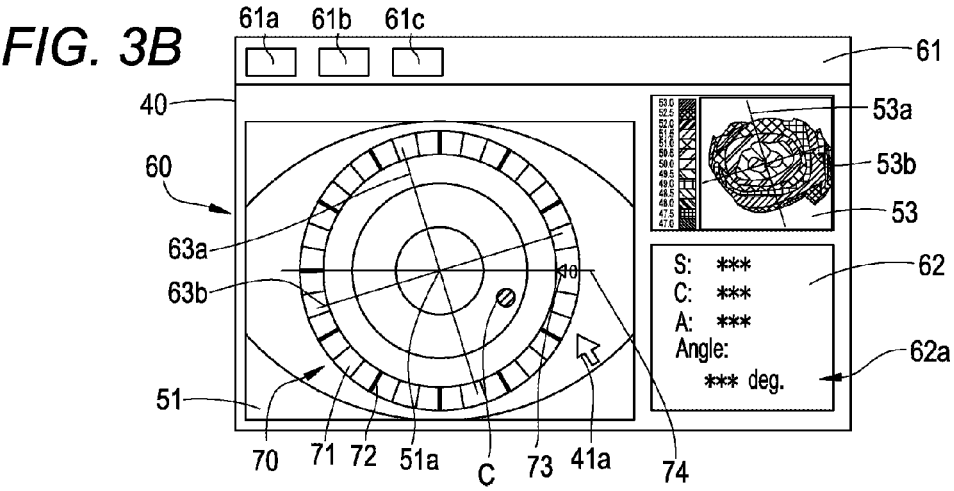
FIG. 3B illustrates the guide creation screen on which a gauge image is displayed.

When the switch 61a is pressed, the control unit 10 makes the gauge image 70 displayed to be superimposed outside the corneal ring of the anterior segment image 51 (refer to FIG. 3B). The gauge image 70 has a base 71, scale marks 72, a reference position 73, and a reference line (reference meridian) 74. The base 71 is in a ring shape centering on the pupil center position 51a. The scale marks 72 are provided on the base 71 and represent angles. The reference position 73 is a reference position representing a 0-degree angle (0-degree reference) out of the scale marks 72. The reference line 74 is a line running on the pupil center position 51a and the reference position 73. The base 71 is in a ring shape to allow the corneal ring or the like of the patient's eye to be displayed therein. This enables the operator to visibly recognize the feature points such as an iris pattern inside the corneal ring and suprascleral capillary vessels outside the corneal ring. The scale marks 72 are provided with the reference position 73 being the 0-degree angle. The scale marks 72 have small scale marks provided at regular intervals (e.g., 10 degrees) and large scale marks at intervals (e.g., 30 degrees) wider than those of the small scale marks. The reference position 73 corresponds to a 0-degree angle position of the actual cornea gauge. The reference line 74 is displayed in different color (e.g., green) from those of the strong principal meridian 63a and the weak principal meridian 63b to facilitate visible recognition of the reference position 73. Positional information of graphics such as lines displayed to be superimposed on the anterior segment image 51 is managed to correspond to a coordinate system of the anterior segment image 51. Thus, the control unit 10 can derive an angle and the like formed by two lines. On the display box 62 is displayed an axial angle (angular difference) 62a of the strong principal meridian 63a to the reference line 74. The control unit 10 calculates a value of the axial angle by converting the meridian of the reference line 74 into 0 degrees and calculating an angle between the reference line 74 and the strong principal meridian 63a however the angle of the reference line 74 is.

That is, on the guide creation screen 60 is displayed the astigmatic axis information of the patient's eye. The astigmatic axis information in the first embodiment is information that enables the operator to recognize the astigmatic axis of the patient's eye easily when the cornea gauge is placed at the anterior segment of the patient's eye. More specifically, the astigmatic axis information is information representing a relationship between the reference position 73 and the astigmatic axis and includes first astigmatic axis information and second astigmatic axis information. The first astigmatic axis information is information to make the astigmatic axis recognized as graphics. The first astigmatic axis information is displayed to be superimposed on the anterior segment image 51 such as the reference position 73, the scale marks 72, and the astigmatic axis (strong principal meridian 63a). The second astigmatic axis information is information to make the astigmatic axis recognized as values. The second astigmatic axis information is information such as the axial angle 62a of the astigmatic axis (strong principal meridian 63a) to the reference line 74 running on the pupil center position 51a and the reference position 73. In the first embodiment, the first and second astigmatic axis information is contained in the guide (gauge image).

The gate image 70 is rotated centering on the pupil center position 51a by dragging the base 71 with the cursor 41a. At this time, the scale marks 72, the reference position 73, and the reference line 74 are rotated in accordance with the rotation of the gauge image 70. At this time, the control unit 10 performs calculation again, updates the value of the axial angle 62a, and displays it on the display box 62a.

Figure 3C:
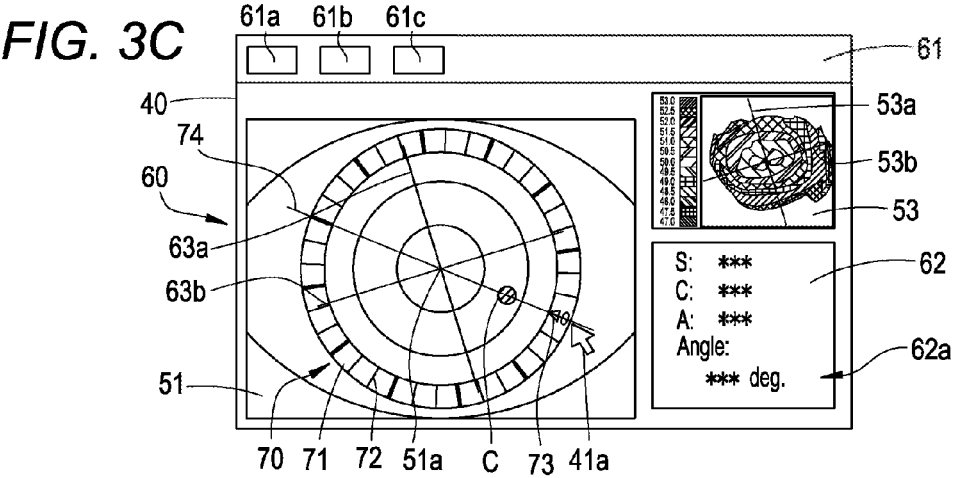
FIG. 3C illustrates the guide creation screen after a feature point has been designated.

The operator rotates the gauge image 70 (moves the reference position 73) such that a feature point C of the iris and the reference position 73 may be aligned with each other as illustrated in FIG. 3C. For example, the operator drags and rotates the gauge image 70 with the cursor 41a. When the dragging with the cursor 41a is finished, the control unit 10 converts the meridian running on the reference position 73 (reference line 74) into the 0-degree meridian based on the coordinate position of the reference position 73. The control unit 10 then calculates the value of the axial angle 62a of the strong principal meridian 63a to the reference line 74 again. The control unit 10 displays the updated axial angle (angular difference) 62a on the display box 62 again. The updated angular difference 62a represents an angular difference between the 0-degree angle position of the cornea gauge and the astigmatic axis (strong principal meridian) of the patient's eye in a case where the reference position of the cornea gauge is placed at the actual position of the feature point C of the patient's eye. Also, the control unit 10 makes rotation of the reference line 74 follow the rotation of the gauge image 70. Consequently, the control unit 10 displays the reference position 73 as the meridian running on the feature point C. By this display processing, the meridian running on the feature point C and the reference position 73 correspond to each other. It is to be noted that the control unit 10 may be configured such that the reference position 71 may move by arranging the cursor 41a around the gauge image 70 and performing clicking.

When the switch 61b is pressed in this state, the guide image (including the value data) displayed on the current guide creation screen 60 is stored in the memory 11. Also, when the switch 61c is pressed, the guide image displayed on the current guide creation screen 60 is printed (output) by the printer 42. The operator can take the printed matter (hard copy of the guide image) into the operation room. The operator can place the cornea gauge at the anterior segment of the patient's eye with reference to the information shown in the guide and perform the operation while recognizing the astigmatic axis of the patient's eye.

In this manner, the operator can designate the reference position 73 for placing the cornea gauge based on the features of the patient's eye. The operator can also obtain the guide instructing the position to place the cornea gauge. Hence, the operator can position and install the toric IOL efficiently when he/she injects the IOL in the patient's eye. By using such a guide, he/she can recognize the astigmatic axis of the patient's eye easily during the operation. That is, positioning of the IOL can be performed efficiently. Also, by placing the cornea gauge to align with the feature point of the patient's eye, the cornea gauge can be replaced to a correct position even when the cornea gauge is misaligned during the operation. This reduces the possibility to install the IOL in a state where the axis of the IOL is misaligned with the astigmatic axis of the patient's eye. Accordingly, a vision correction result after the operation improves. Also, showing the angular difference 62a in a state where the reference position 73 is always at the 0-degree angle can make it clear how many degrees the astigmatic axis of the patient's eye is tilted from the reference position of the cornea gauge. This can reduce confusions during the operation. Also, using the guide created by the ophthalmic apparatus 100 dispenses with a work of putting a mark directly on the sclera or the like of the patient's eye to recognize the astigmatic axis. This can reduce a burden on the patient.

Figure 4A:
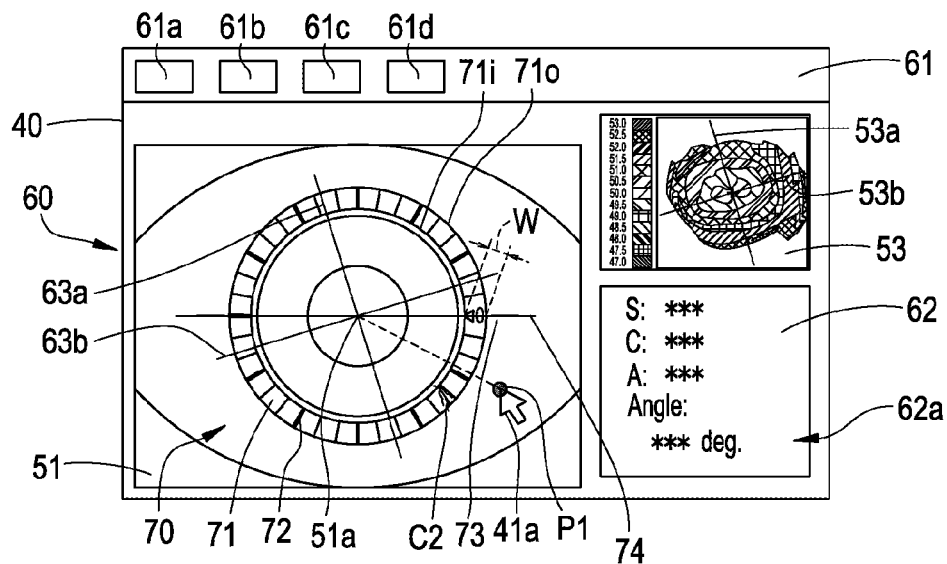
FIG. 4A illustrates a guide creation screen in a second embodiment of the ophthalmic apparatus.
Figure 4B:
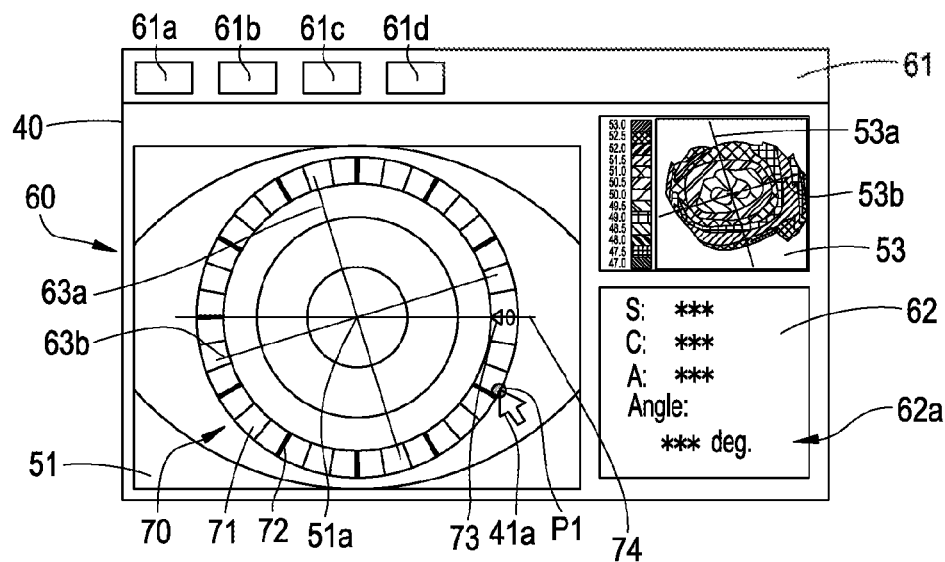
FIG. 4B illustrates the guide creation screen on which a size of a gauge image has been changed.

Next, a second embodiment of the ophthalmic apparatus will be described. The ophthalmic apparatus as the second embodiment has a function to adjust the size of the gauge image displayed to be superimposed on the patient's eye on the guide creation screen to fit with the patient's eye in addition to the functions of the aforementioned first embodiment. FIGS. 4A and 4B illustrate monitor screens in the second embodiment. FIG. 4A illustrates a state of the gauge image 70 before the size change, and FIG. 4B illustrates a state of the gauge image 70 after the size change.

As illustrated in FIG. 4A, on the bar 61 of the guide creation screen 60 is further displayed a switch 61d to input a signal for changing the size (display size) of the gauge image 70. The control unit 10 gets into a state (mode) of changing the size (diameter of the circumference) of the gauge image 70 based on the input signal from the switch 61d. When the control unit 10 receives the input signal from the switch 61d, the control unit 10 superimposes and displays the gauge image 70 having a standard size (diameter) on the anterior segment image 51. The control unit 10 also serves as a size changing unit. When a designation signal is input at a certain position on the anterior segment image 51, the control unit 10 changes the size (diameter) of the gauge image 70 in a state of fixing the center position of the gauge image 70 based on the information on the position at which the designation signal has been input (e.g., XY coordinates).

For example, there is a feature point C2 such as vessels at the sclera part of the anterior segment image 51. When the gauge image 70 having the standard size remains displayed to be superimposed on the anterior segment image 51, the feature point C2 is difficult to confirm. Thus, the control unit 10 enlarges the gauge image 70 such that the feature point C2 may be easy to confirm. This makes it easy to designate the feature point.

More specifically, a position P1 is designated by means of the cursor 41a, for example. In response to this, the control unit 10 calculates a distance R1 (length of the straight line shown in a dotted line) between the pupil center position 51a and the position P1. The control unit 10 regards the distance R1 as a diameter (here, as a radius) of the circumference of the gauge image 70. The control unit 10 then changes the size of the gauge image 70 with reference to an outer circumference 71o of the base 71. The control unit 10 changes the display size of the gauge image 70 in a state of fixing the pupil center position 51a. The control unit 10 superimposes and displays the gauge image on the anterior segment image 51 such that the radius of the outer circumference 71o of the base 71 may correspond to the distance R1 centering on the pupil center position 51a. To prevent the gauge image 70 that has changed in size from departing from the actual cornea gauge, a width W of the base 71 (difference between the outer circumference 71o and an inner circumference 71i of the base 71) is constant. The control unit 10 changes the amount of a radius of the inner circumference 71i as much as the changing amount of the radius of the outer circumference 71o. The control unit 10 also changes the interval of the scale marks 72 in accordance with the change of the size of the base 71. It is to be noted that the number of the scale marks 72 may be increased or decreased with the interval of the displayed scale marks 72 constant.

Similarly, the size of the gauge image 70 can be reduced by changing a designation position of the cursor 41a.

In this manner, by designating a position on the screen, the size of the gauge image 70 is changed. By doing so, the operator (examiner) can confirm a feature point that is overlapped with the gauge image 70 easily. Also, a diameter of the corneal ring differs with each patient's eye. Nevertheless, the size of the gauge image can be changed easily. Accordingly, the gauge image can be placed around the corneal ring of the patient's eye.

It is to be noted that, in the above description, the diameter of the circumference of the gauge image 70 is set with reference to the outer circumference of the base 71. However, the reference for the diameter of the circumference of the gauge image 70 is not limited to this. The reference can be anything as long as it is a circumference that can be a reference at the time of changing the size of the gauge image 70. For example, it can be the inner circumference of the base 71 or a circumference running on the center of the base 71.

It is to be noted that, in the above description, the size change of the gauge image 70 is performed by the position designation by the operator. However, a trigger of the size change is not limited to this. The size change of the gauge image 70 has only to be done such that the feature point can be easily confirmed in a state where the gauge image 70 is displayed to be superimposed on the anterior segment image. For example, the size of the gauge image 70 may be changed (adjusted) without waiting for an input by the operator. In this case, the control unit 10 performs image processing of the anterior segment image 51, extracts the ring, and derives the diameter of the ring. The control unit 10 adds a pre-set value to the diameter of the ring to derive the size of the gauge image 70. The control unit 10 then superimposes and displays the gauge image 70 that has changed in size on the anterior segment image 51.

It is to be noted that the size change of the gauge image 70 may be performed by dragging by means of the cursor 41a. In this configuration, the cursor 41a is moved outward (in a direction away from the pupil center position 51a) in a state where the gauge image 70 is dragged by means of the cursor 41a. As a result, the gauge image 70 is (displayed to be) enlarged in concert with the movement of the cursor 41a. Similarly, when the cursor 41a is moved inward, the gauge image 70 is shrunk. The control unit 10 detects (monitors) the position of the cursor 41a dragging the gauge image 70 and controls size calculation and display of the gauge image 70.

Figure 5:
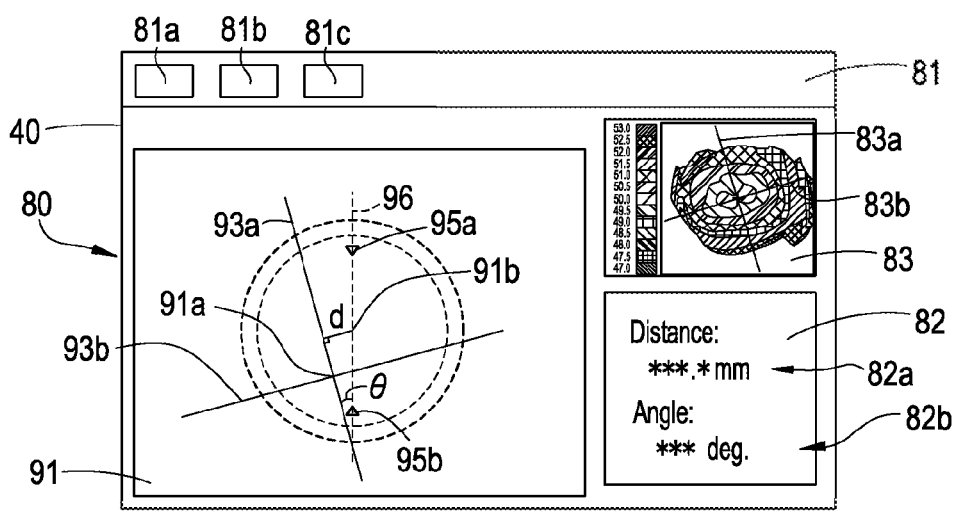
FIG. 5 illustrates a postoperative evaluation screen in a third embodiment of the ophthalmic apparatus.

Next, a third embodiment of the ophthalmic apparatus will be described. The ophthalmic apparatus as the third embodiment has a function to evaluate a state of the patient's eye after the toric IOL has been installed (postoperative state). FIG. 5 illustrates a postoperative evaluation screen of the patient's eye. It is to be noted that the patient's eye has been provided with the toric IOL, and the pupil has been dilated.

On a postoperative evaluation screen 80 are arranged a bar 81 on which various switches are arranged, a display box 82, a map 83, and a retro-illumination image 91. The bar 81 has a switch 81a, a switch 81b, and a switch 81c. The switch 81a is a switch to input a signal for obtaining (measuring) and displaying the retro-illumination image 91 of the patient's eye and the astigmatic axis of the cornea. The switch 81b is a switch to input a signal for moving to a mode to define an axis of the toric IOL. The switch 81c is a switch to input a signal for moving to a mode to derive a difference between the astigmatic axis of the cornea and the axis of the toric IOL (here, an angular difference and a distance).

The retro-illumination image 91 is obtained by imaging by the camera 20 an image of a crystalline lens part (pupil part) of the patient's eye illuminated by the light source of the measurement portion 30. The control unit 10 projects the illumination light to the fundus of the patient's eye from the light source of the measurement portion 30 based on the instruction signal. The camera 20 images the crystalline lens illuminated from the backside by the light reflected on the fundus. By doing so, a state of a light transmitting part (especially, the crystalline lens) of the patient's eye is captured as an image. Thus, a part outside the pupil is imaged darkly. It is to be noted that the anterior segment containing the sclera, the iris, and the like and the retro-illumination state of the crystalline lens may be captured as an image simultaneously.

When the switch 81a is pressed, the control unit 10 images the retro-illumination image 91 and obtains the astigmatic axis data of the cornea of the patient's eye (the dioptic power and the axial angle of the strong principal meridian and the dioptic power and the axial angle of the weak principal meridian) similarly to the above description. The retro-illumination image 91 and the astigmatic axis data are stored in the memory 11. On the postoperative evaluation screen 80, the retro-illumination image 91 is displayed. On the retro-illumination image 91 on the screen 80 are displayed to be superimposed a strong principal meridian 93a and a weak principal meridian 93b centering on an optical axis (corneal apex) 91a of the camera 20. Also, on the map 83 are displayed to be superimposed a strong principal meridian 83a and a weak principal meridian 83b similarly to the above description.

When the switch 81b is pressed, the control unit 10 allows designation of feature points by the cursor 41a. Around an edge of an optical portion (the dotted circle in the figure) of the toric IOL are provided two marks that represent the axis to be opposed to each other. On the retro-illumination image 91 are displayed marks 95a and 95b that represent the axis of the toric IOL. When the marks 95a and 95b are selected by the cursor 41a, the control unit 10 derives a straight line running on the marks 95a and 95b. The control unit 10 then superimposes and displays an axis 96 on the retro-illumination image 91.

When the switch 81c is pressed, the control unit 10 calculates a difference between the strong principal meridian 93a and the axis 96. The control unit 10 displays a distance d (described later) between the two straight lines in a distance display column 82a and an angle θ formed by the two straight lines in an angle display column 82b. The control unit 10 performs image processing of the retro-illumination image 91 to derive a pupil center position 91b. The pupil center position 91b is derived as a center of a circle of the pupil (brightness border part on the retro-illumination image). The control unit 10 regards a length of a perpendicular drawn from the pupil center position 91b to the strong principal meridian 93a as a difference (distance d) between the strong principal meridian 93a and the axis of the toric IOL (axis 96). The distance d corresponds to a distance between the axis 96 turned centering on the pupil center position 91b until it is parallel to the strong principal meridian 93a and the strong principal meridian 93a (distance of a perpendicular drawn from the turned axis 96 to the strong principal meridian 93a). It is to be noted that a distance between the optical axis 91a and the pupil center position 91b may be displayed in the distance display column 82a. The control unit 10 derives an angular difference of the axis 96 with reference to the strong principal meridian 93a. Accordingly, a positive or negative value is displayed in the angle display column 82b.

From the distance d and the angle θ displayed on the display box 82, the examiner can confirm an installation state of the toric IOL quantitatively. For example, the operator (examiner) can confirm positioning accuracy at the time of installing the toric IOL by confirming the angular difference between the axis of the toric IOL and the astigmatic axis of the cornea. The operator can also evaluate the extent of misalignment of the center position of the astigmatic axis (corneal apex) with the pupil center position by confirming the relationship between the distance d and the patient's postoperative vision. By confirming several examples, the operator will figure out the distance d that allows prescription for the toric IOL. In other words, the operator can evaluate if the toric IOL can be applied based on the difference between the corneal apex and the pupil center position. By storing and analyzing data of the distance d, the operator can set a criterion for judgment of whether or not the toric IOL can be prescribed.

In this manner, positioning of the toric IOL to the patient's eye can be performed efficiently. In this case, the postoperative evaluation screen 80 serves as a guide at the time of installing the toric IOL efficiently (applying the toric IOL to the operation).

Meanwhile, in the above description, the angle θ formed by the strong principal meridian 93a and the axis 96 is displayed the angle display column 82b. However, in addition to these displays, scale marks (gauge) arranged in a circular shape centering on the corneal apex or the pupil center may be displayed to be superimposed on the retro-illumination image 91. In this case, the examiner visually confirms the angular difference between the strong principal meridian 93a and the axis 96.

Also, in the above description, the angular difference between a straight line 95 (axis of the intraocular lens) and the strong principal meridian 93a (astigmatic axis of the cornea) is displayed in the angle display column 82b as the angle θ. However, the embodiment is not limited to this configuration, and respective angles of the straight line 95 and the strong principal meridian 93a (for example, angles to a horizontal axis of the patient's eye) may be displayed in the angle display column 82b.

Also, the angle display column 82b may not be provided. In a case where the gauge image 70 is to be displayed on the retro-illumination image as described above, the examiner can confirm the astigmatic axis of the cornea and the axis of the intraocular lens by the scale marks of the gauge image 70. Also, the distance display column 82a may not be provided. The postoperative evaluation screen 80 has only to be configured to allow the examiner to confirm at least the astigmatic axis of the cornea and the axis of the intraocular lens.

Also, in the above description, the distance d and the like are derived, regarding the pupil center position 91b as a center (reference) of the intraocular lens. However, the embodiment is not limited to this configuration, and the distance d and the like may be derived centering on an optical axis of an optical portion of the intraocular lens. For example, a midpoint of the marks 95a and 95b on the straight line running on the marks 95a and 95b (axis of the intraocular lens) is set as a center position. The control unit 10 derives the aforementioned midpoint from the position of the mark 95a and the position of the mark 95b to obtain an optical center position 91b (in this case, the pupil center position and the optical center position correspond to each other).

Also, in the above description, the marks 95a and 95b are designated by operation of the examiner. However, the embodiment is not limited to this configuration, and the control unit 10 may designate the marks 95a and 95b automatically by image processing or the like.

Meanwhile, when the gauge image 70 is displayed, the base 71 and the reference line 74 may not necessarily be displayed. Also, the scale marks 72 may not be displayed over the entire circumference. Also, the reference position 73 may not necessarily be displayed on the gauge image 70. The reference position 73 may be displayed on the iris or the sclera of the anterior segment image as long as the feature points can be designated easily, and the reference position can be visibly recognized easily.

Meanwhile, in the first to third embodiments, the map 53, the display box 62, and the like as well as the anterior segment image 51 are displayed as the guide. However, the embodiment is not limited to this configuration, and at least the astigmatic axis of the patient's eye, the feature point C of the anterior segment image 51, and the gauge image 70 have only to be displayed as the guide. Alternatively, the anterior segment image 51 on which the gauge image 70 and the like are displayed may be used as the guide. Also, as for the astigmatic axis of the patient's eye, both the strong principal meridian and the weak principal meridian may not be displayed. Either the strong principal meridian or the weak principal meridian has only to be displayed as long as a meridian as a reference for positioning of the IOL is recognizable.

Also, in the first to third embodiments, the center position of the anterior segment of the patient's eye (center position of the gauge image) is regarded as the pupil center position 51a obtained from the anterior segment image 51. However, the embodiment is not limited to this configuration, and the center position of the gauge image may be regarded as the optical axis center of the imaging optical system in the camera 20.

Also, in the first to third embodiments, the reference line is displayed, aligning the reference position with the feature point. However, the embodiment is not limited to this configuration, and the reference position and a 0-degree meridian of the anterior segment image may be displayed to correspond to each other. In this case, the 0-degree meridian of the anterior segment image is a straight line running on the pupil center position parallel to an x coordinate of the image, for example. The axial angle is calculated and displayed as an angle of the reference line to the 0-degree meridian of the anterior segment image.

Also, in the first to third embodiments, the ophthalmic apparatus 100 obtains the anterior segment image data astigmatic axis data, and the like of the patient's eye. However, the embodiment is not limited to this configuration, and a program for executing the processing described in the first to third embodiments may be installed in a general-purpose computer, the anterior segment image data, astigmatic axis data, and the like may be obtained by separate apparatuses and input in the computer, and the guide may be created. An example of the computer is a personal computer including a memory storing the program, a CPU as an execution member (execution unit) of the program, an operation unit, a monitor, and the like. In this case, the data for the center position of the anterior segment of the patient's eye may be input in the computer. In a case where the center position of the anterior segment of the patient's eye is regarded as the pupil center position, the pupil center position may be derived from the anterior segment image by image processing on the computer.

Also, in the first to third embodiments, the guide is printed out by use of the printer. However, the embodiment is not limited to this configuration, and the guide may be output by use of a display unit such as a monitor. The guide has only to be output such that the operator can confirm it during the operation. Also, an output destination of the guide may be an external memory, another unit on the network, and the like.

Meanwhile, in the first to third embodiments, the operator designates the reference position (feature point) manually. However, the embodiments are not limited to this configuration, and the reference position may be designated automatically by use of known image processing techniques. For example, the feature point around the corneal ring of the anterior segment image is detected (extracted) by the image processing. A criterion for detection is a high-contrast and large-size feature point to the extent visibly recognizable. In a case where there are plural feature points of this kind, they may be ranked in terms of the contrast, size, and the like, and one that is visibly recognizable may be designated, or the operator may select one.

It is to be understood that various modifications of the foregoing embodiments can be done. The first to third embodiments shall include such modifications within the range of the same technical spirit.

While the embodiments have been illustrated and described in detail, the foregoing description is in all aspects illustrative and not restrictive. It is therefore understood that numerous modifications and variations can be devised without departing from the spirit and scope of the embodiments.

What is claimed is:

1. An ophthalmic apparatus for guiding positioning an intraocular lens for astigmatism correction, comprising:
    an obtaining unit for obtaining an anterior segment image of a patient's eye and an astigmatic axis of a patient's cornea; and
    a display control unit for superimposing and displaying, on the anterior segment image of the patient's eye, a meridian based on the astigmatic axis of the cornea and serving as a reference for positioning a toric intraocular lens, and a line passing through a feature point included in the anterior segment image of the patient's eye, and for displaying the meridian and the line on a monitor such that an angle of the meridian relative to the line is recognizable an anterior segment imaging optical system for obtaining an anterior segment image of the patient's eye; and
    an analyzing unit for measuring a cornea shape distribution of the patient's eye and the astigmatic axis of the cornea by analyzing the anterior segment image including a ring image, the anterior segment image being obtained by the anterior segment imaging optical system,
    wherein the display control unit superimposes and displays, on the anterior segment image of the patient's eye, a meridian based on the astigmatic axis of the cornea obtained by the analyzing unit and serving as a reference for positioning the toric intraocular lens, and a line passing through a feature point included in the anterior segment image of the patient's eye obtained by the anterior segment imaging optical system, and displays the meridian and the line on the monitor such that an angle of the meridian relative to the line is recognizable.

2. The ophthalmic apparatus according to claim 1,
    wherein the display control unit controls a touch panel serving as the monitor to display the anterior segment image of the patient's eye on which the meridian and the line have been superimposed and displayed, and
    the display control unit rotates the line at an arbitrary rotation angle relative to the anterior segment image of the patient's eye, based on an operation signal from the touch panel.

3. The ophthalmic apparatus according to claim 1,
    wherein the display control unit displays the line and the meridian in different colors, respectively.

4. The ophthalmic apparatus according to claim 1,
    wherein the display control unit displays, on the monitor, a color map indicating the cornea shape distribution of the patient's eye obtained by the analyzing unit.

5. The ophthalmic apparatus according to claim 1,
    wherein the display control unit superimposes and displays, on the anterior segment image of the patient's eye, a meridian corresponding to either a strong principal meridian or a weak principal meridian of the astigmatic axis of the cornea obtained by the analyzing unit, and the line passing through a feature point included in the anterior segment image of the patient's eye obtained by the anterior segment imaging optical system.

* * * * *